United States Patent [19]
Danon

[11] Patent Number: 5,348,001
[45] Date of Patent: Sep. 20, 1994

[54] OXYGEN BREATHING CONTROLS

[75] Inventor: Joseph S. Danon, Los Angeles, Calif.

[73] Assignee: American Safety Flight Systems, Inc., Glendale, Calif.

[21] Appl. No.: 929,701

[22] Filed: Aug. 12, 1992

[51] Int. Cl.⁵ .............................................. A62B 9/02
[52] U.S. Cl. .......................... 128/205.24; 128/204.18;
128/204.26; 137/486; 137/505.36
[58] Field of Search .......................... 137/486, 505.36;
128/205.24, 204.18, 204.26, 204.29, 205.22,
202.11; 600/20

[56] References Cited

U.S. PATENT DOCUMENTS

| | | | |
|---|---|---|---|
| 2,333,775 | 11/1943 | Gille | 137/505.36 |
| 4,163,448 | 8/1979 | Grouard | 128/205.24 X |
| 4,297,998 | 11/1981 | Christianson | 128/204.26 |
| 4,409,978 | 10/1983 | Bartos | 128/205.12 |
| 4,436,090 | 3/1984 | Darling | 128/204.26 |
| 4,567,915 | 2/1986 | Bates | 138/42 |
| 4,651,728 | 3/1987 | Gupta | 128/201.28 |
| 4,799,476 | 1/1989 | McGrady | 128/202.11 |
| 4,838,257 | 6/1989 | Hatch | 128/204.18 |
| 4,850,345 | 7/1989 | Jackson | 128/202.27 |
| 4,858,606 | 8/1989 | Hamlin | 128/204.29 |
| 4,960,119 | 10/1990 | Hamlin | 128/204.18 |
| 5,007,420 | 4/1991 | Bird | 128/200.14 |

FOREIGN PATENT DOCUMENTS 1750093 7/1978 Fed. Rep. of Germany ........................ 137/505.36

OTHER PUBLICATIONS

U.S. application Ser. No. 07/739,595, filed Aug. 1, 1991, Danon.
U.S. application Ser. No. 07/930,149, filed Aug. 13, 1992, Danon.
U.S. application Ser. No. 07/932,715, filed Aug. 20, 1992, Danon.

Primary Examiner—Edgar S. Burr
Assistant Examiner—Eric Raciti
Attorney, Agent, or Firm—Graham & James

[57] ABSTRACT

The oxygen breathing control of the present invention for supplying oxygen to a user employs a first stage regulation module, a valving module which couples with the first stage regulation module, a servo regulator module and an aneroid module. The servo regulator module with oxygen conservation function during exhalation controls oxygen flow between zero to approximately 34,000 feet, and the aneroid module takes over the control of breathing pressure schedule between 34,000 to 45,000 feet. A flow restrictor screw module is employed in the passage between a control chamber and an inlet chamber of the valving module for regulating the flow between the two chambers.

10 Claims, 6 Drawing Sheets

OXYGEN BREATHING CONTROLS

FIELD OF THE INVENTION

This invention relates generally to oxygen supply systems, and more particularly to oxygen breathing controls which supply oxygen to users in a low oxygen-level environment such as at a high altitude.

BACKGROUND OF THE INVENTION

Oxygen breathing controls are normally used to supply oxygen to users at high altitudes. Common users are parachutists and airborne military personnel in an unpressurized aircraft. A user aboard an unpressurized aircraft has the use of an oxygen supply tank, i.e., aircraft-mounted prebreather. A pre-breather system supplies 100% oxygen to the user which serves to denitrify the user's blood. Utilization of the aircraft-mounted system also conserves parachutist's personal oxygen supply for a later use during a parachute descent. Before exiting the aircraft, the parachutist switches from an aircraft-mounted prebreather to his/her personal oxygen supply.

A cabin crew member user who must perform duties during a flight may use a portable oxygen system for mobility within the aircraft cabin or may access to an aircraft-mounted prebreather to conserve oxygen in the personal supply.

Conventional control systems have many areas that need improvements. An existing unit is CRU-79/P which is a chest mounted, 100% oxygen, positive pressure regulator. A majority of conventional regulators use a spring-loaded diaphragm/poppet/guide/seat arrangement. Such a mechanical design has inherent problems with a leakage when closed which is caused by a poorly seated poppet. For example, the conventional diaphragm often has an asymmetric contact with a related body seal and imprecise guide into which a diaphragm stem could move. Further, the spring loading the conventional diaphragm weakens.

Prior art breathing regulators have a problem in that approximately 10% volume is lost to the atmosphere. A conventional breathing regulator continuously bleeds oxygen to atmosphere even when it is not in use. The bleeding loss continues as long as the breathing regulator is connected to an oxygen source. The bleed rate can be approximately 0.75 lpm. Under normal breathing conditions, a breather consumes approximately 8 lpm. Thus, a 0.75lpm bleed rate represents approximately a 10% volume loss to atmosphere. For a parachutist who must descent from a high altitude with a personal oxygen cylinder of relative low volume, a loss of 10% oxygen volume could have a significant effect.

Therefore, it is an object of the present invention to provide an oxygen breathing control which facilitates its manufacturing, stocking, assembly and testing processes. One of the objects of the present invention is to provide an oxygen breathing control having a valving module containing no mechanical moving parts. Another object of the present invention is to provide a pneumatic valving module. Yet another object of the present invention is to provide an oxygen breathing control having a valving module which does not leak when fully closed. Another object of the present invention is to provide a valving module which is sensitive to breathing pressure changes and has a valve liner with a long service life. It is one of the objects of the present invention to provide an oxygen breathing control which is oxygen efficient. It is also an object of the present invention to provide an aneroid which controls breathing pressure schedule at a higher altitude of 34,000 to 45,000 feet.

Other improvements and benefits and usefulness of the present invention will become apparent as a reader proceeds through the explanations below.

SUMMARY OF THE INVENTION

The oxygen breathing control of the present invention provides a first stage regulation module, a valving module, a flow restrictor screw, a servo regulator module and an aneroid module. The present invention is also provided with a threaded mount, a relief valve module, an inlet adapter assembly module and a cap assembly.

The first stage regulation module disposed at the inlet opening of the oxygen breathing control is capable of supplying oxygen with a nominal pressure and shutting off an oxygen supply during the exhalation portion of the breathing cycle, thereby conserving oxygen. The valving module of the present invention provides a balanced valve design which is sensitive to differential pressures. Since the valving module is pneumatic, it does not have the leakage problem the conventional mechanical system does.

Further, the servo regulator module of the present invention also conserves oxygen. It does this by internally bleeding oxygen to the outlet chamber, and not to atmosphere at least up to 34,000 feet. Beyond approximately 34,000 feet, the servo regulator mechanism is taken over by the aneroid module which controls the breathing pressure schedule. The present invention is provided with a two-control adjustment flexibility which conventional systems did not have.

DETAILED EXPLANATION OF THE INVENTION

Under normal use, the oxygen breathing control of the present invention supplies oxygen rich gas or 100% oxygen to parachutists and airborne military personnel in an unpressurized aircraft. The oxygen breathing control is designed to serve the users at breathing flow demand rates of 0-200 slpm up to 34,000 feet. At approximately 34,000 feet to 45,000 feet, the oxygen breathing control supplies a scheduled positive pressure of 100% oxygen having pressure between 1.5" $H_2O$ and 20.0" $H_2O$ respectively.

One of the groups of users for which the present invention is intended is a high altitude parachutist group. Parachutists use the oxygen breathing control connected to a personal portable oxygen system during a parachute descent from a high altitude. While in an unpressurized aircraft, the portable supply is normally shut off and the oxygen breathing control is connected to a 100% oxygen console used for prebreathing via an adapter assembly on the oxygen breathing control. Parachutists breathe the 100% oxygen from the console until they are ready to jump from the aircraft at which point the console is turned off and the personal portable supply is turned on.

During the descent down to approximately 34,000 feet, the oxygen breathing control of the present invention automatically supplies 100% oxygen per pressure schedule due to the action of an altitude sensing aneroid. From 34,000 feet to sea level, the oxygen breathing control delivers 100% oxygen upon user's demand at a slight positive pressure. To prevent suffocation, if parachutist's oxygen supply is depleted and he is unconscious, he can still breathe ambient air through an anti-suffocation valve that is an integral part of the inlet adapter assembly.

FIG. 1

Figure 1:
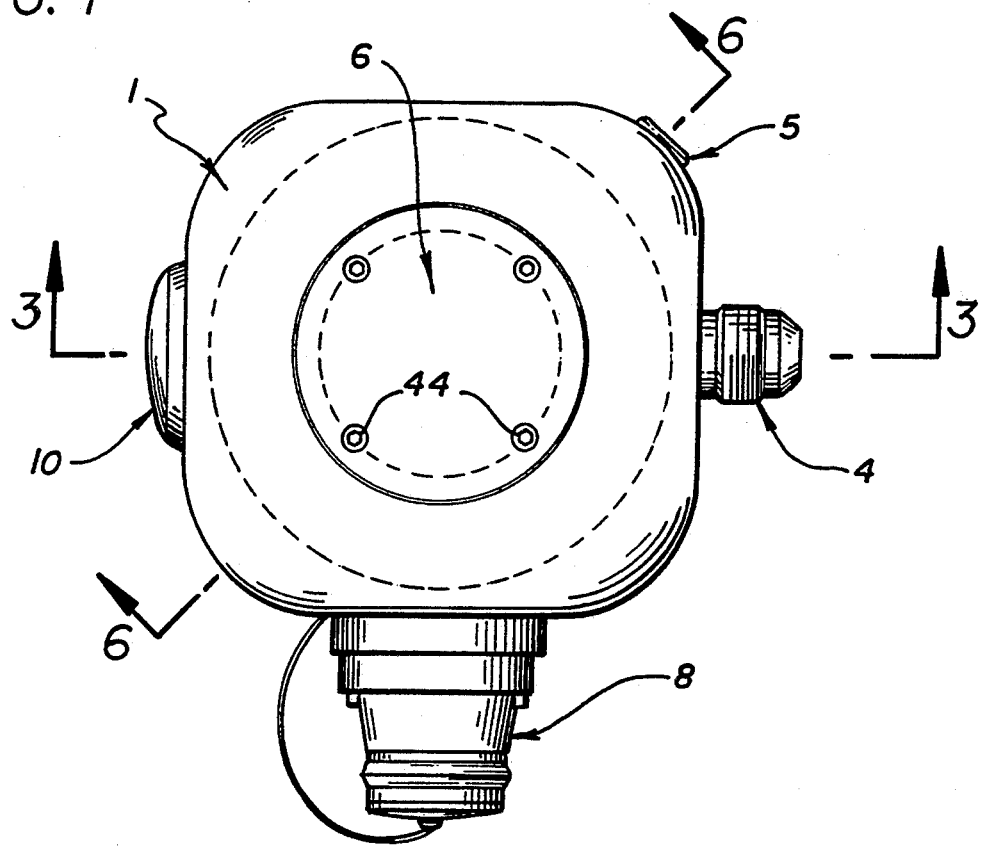
FIG. 1 shows an exterior view of an oxygen breathing control of the present invention.

FIG. 1 shows an external view of the oxygen breathing control of the present invention. The oxygen breathing control device of the present invention has a body 1 which incorporates an outlet connector 2 as shown in FIG. 4, a dovetail mount shown in FIG. 3, a first stage regulation module 73 whose detailed sectional view is provided in FIG. 2. The control is further provided with an inlet valve module 4, a flow restrictor screw module 5, a servo regulator module 6, an aneroid module 7, an inlet adapter assembly module 8, a cap assembly 9 and a relief valve module 10 as seen in FIGS. 1, 3, 4, 5, 6 and 8. The control of the present invention is unique in that it is completely pneumatic and does not involve any mechanical linkages in the dynamically functional modules.

Body

Figure 3:
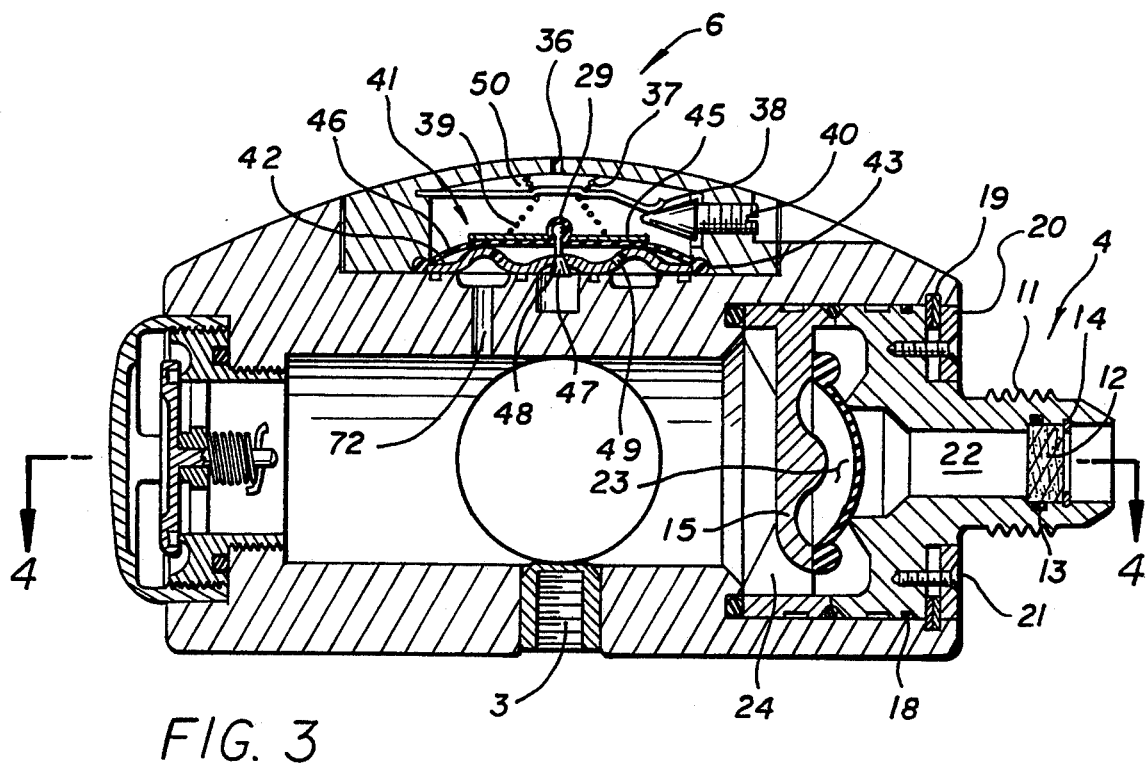
FIG. 3 shows a cross-sectional view of the oxygen breathing control of the present invention showing a servo regulator module and a valving module.
Figure 5:
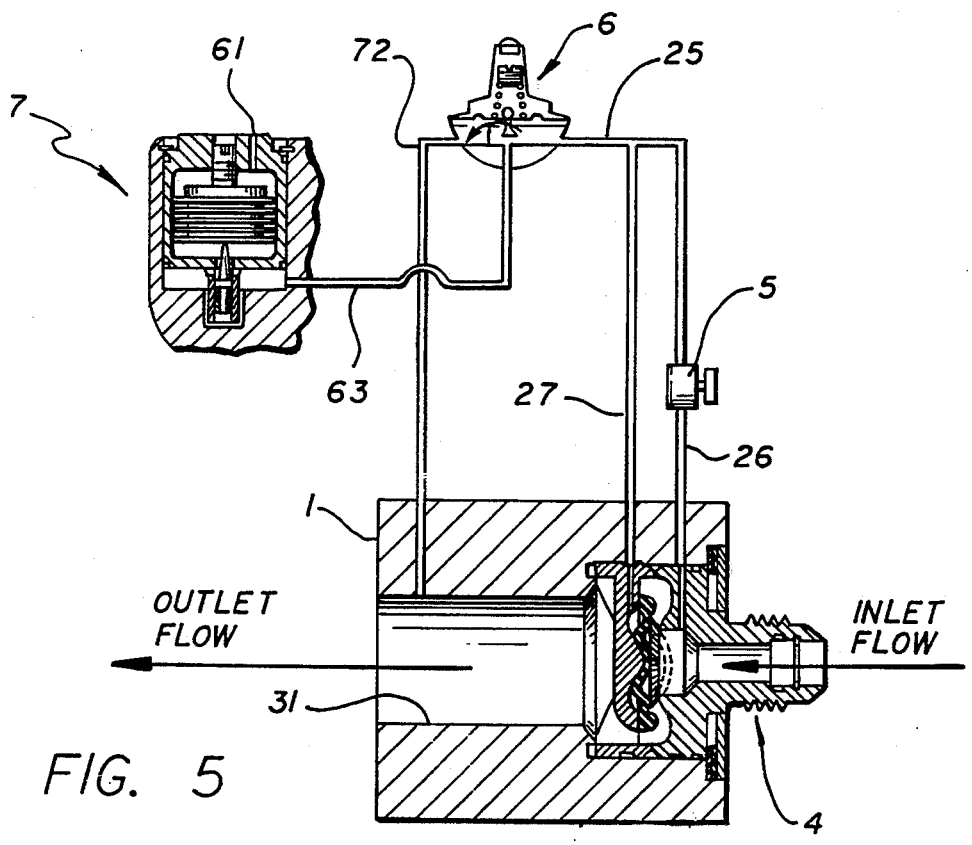
FIG. 5 is a schematic diagram for servo-control loop of the present invention.
Figure 4:
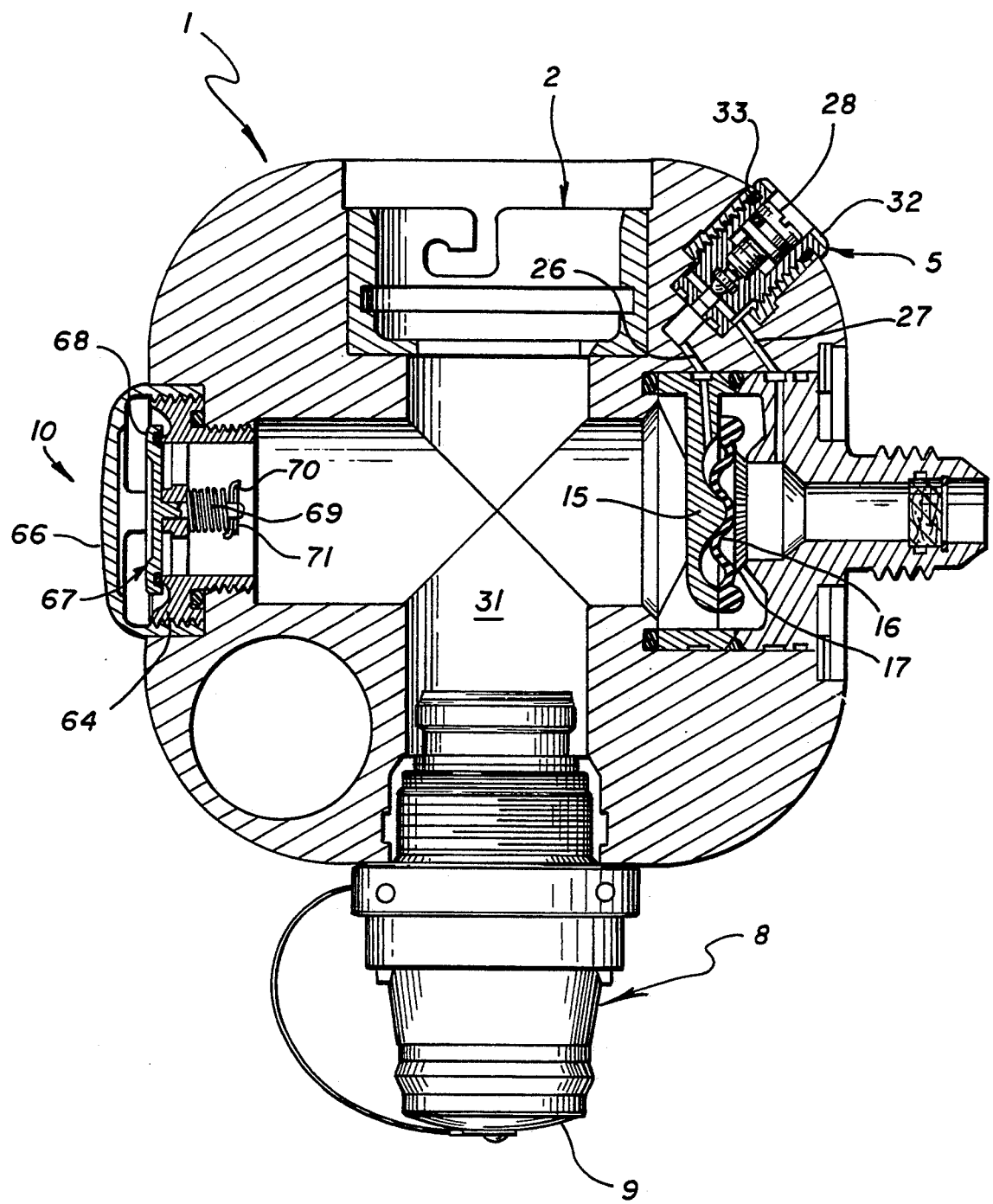
FIG. 4 shows another cross-sectional view of the oxygen breathing control of the present invention showing the flow restrictor screw module, the valving module and a relief valve module.

The threaded mount 3 and the outlet connector 2 in FIGS. 3 and 4 are molded into the body 1 during manufacturing of the body. A user-supplied connection, when secured to the mount 3 provides for an attachment of the control to the parachutist's torso harness or clothing. The outlet connector 2 mates with a conventional 3-pin bayonet connector used with oxygen breathing hoses.

Figure 2:
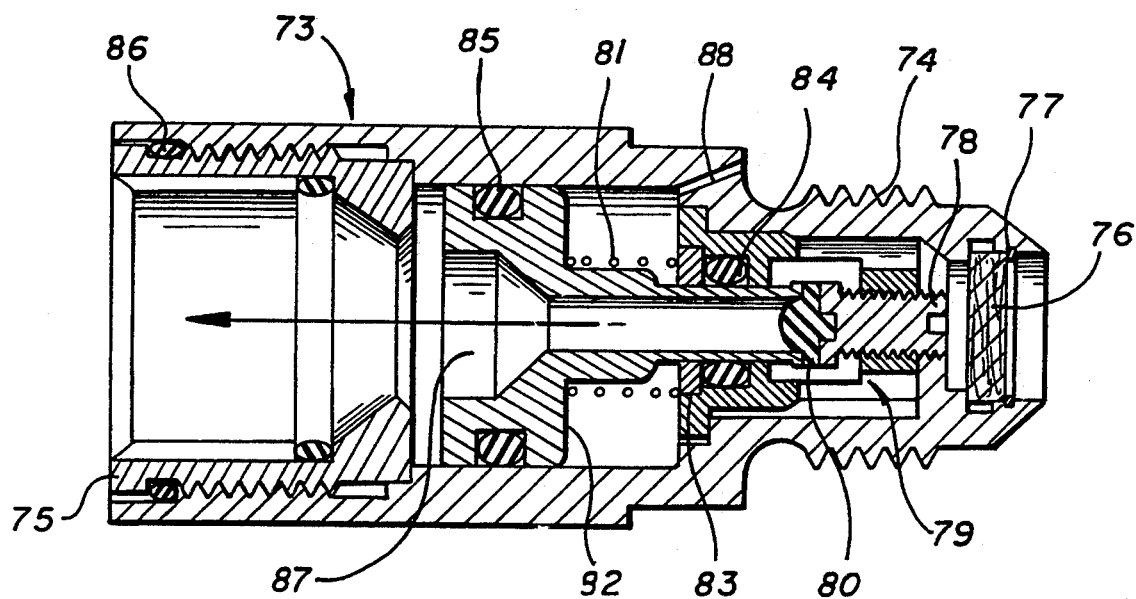
FIG. 2 shows a cross-sectional view of a first stage regulation module of the present invention.

First stage regulation module : FIG. 2.

The oxygen breathing control of the present invention provides a first stage regulation module 73 of FIG. 2 comprising an inlet housing 74 and a sleeve 75 that contain a filter 76, a retaining ring 77, a flow screw 78, an inlet valve 79, a molded seat 80, a pressure regulating spring 81, a piston 82, a retainer 83 and an arrangement of packings 84, 85, 86. The filter 76 is kept in place in the inlet housing 74 by the retaining ring 77. The molded seat 80 is bonded in place on the end of the flow screw 78. The end of the piston shaft and the molded seat 80 form the inlet valve 79 of the module. The retainer 83, staked in place in the inlet housing 74, keeps the packing seal around the shaft of the piston 82 in place and also forms a seat for the pressure regulating spring 81. The sleeve 75 is staked in place in the inlet housing 74. The sleeve 75 is threaded for connection to the valving module 4. The packings 84, 85, 86 prevent an internal and an external leakage of oxygen.

The first stage regulation module 73 operates in three modes. When no oxygen pressure is applied to the first stage regulation module 73, which is a non-operative dormant condition, the pressure regulating spring 81 pushes the head of the piston 82 and fully opens the end of the piston 82 away from the molded seat 80 on the flow screw 78. Until an oxygen pressure is applied to it, the module stays in a dormant condition.

When an oxygen pressure is applied to the module, the module will be in a closed or lockup condition. FIG. 2 shows the first stage regulation module 73 in the lockup condition. Assume a pressure as nominal as 50 psig is applied to the module but there is no breathing, i.e., no oxygen flow demand, by the user. The flow with 50 psig oxygen pressure passes through the filter 76 and openings in the inlet housing 74 and comes to the end of the piston 82 which is separated from the molded seat 80. The inlet valve 79 is open. Oxygen flows through the inlet valve 79, inside an piston chamber 87 and an inlet chamber 22 of a valving module 4, which is presently in a fully closed condition. When pressure in the piston chamber 87 and the inlet chamber 22 of the valving module 4 reaches 20" $H_2O$, it forces the piston 82 toward the flow screw 78, shutting off flow through the inlet valve 79. The closing action, i.e., lock up, is created due to the ratio of surface areas on piston 82. Ratio of the stem area to the piston head area is 1:70, and the pressure is inverse to this ratio. Hence, 50 psig input results in substantially 20" $H_2O$ pressure in the inlet chamber 22 and the piston chamber 87. The lockup condition lasts until the user demands flow.

Inhalation by the user initiates the third mode of the module, a breathing cycle. The pressure conditions which prevail in the inlet chamber 22 of the valving module 4 are imposed in the piston chamber 87 of the first stage regulation module 73. Accordingly, the valving action i.e., opening and closing of the inlet valve 79 is in tandem with the valving action of a valve liner 16 in valving module 4.

The first stage regulation module of the present invention which regulates the first stage of the pressure regulation of the entire control is unique. The module incorporates a balanced piston design and delivers an outlet pressure of 20" $H_2O$ from a nominal input pressure of 50 psig (ratio of 1:70). In lockup phase of the operation where the user exhales and makes no oxygen flow demand, the first stage regulation module 73 shuts off the flow, thereby conserving oxygen.

Figure 3A:
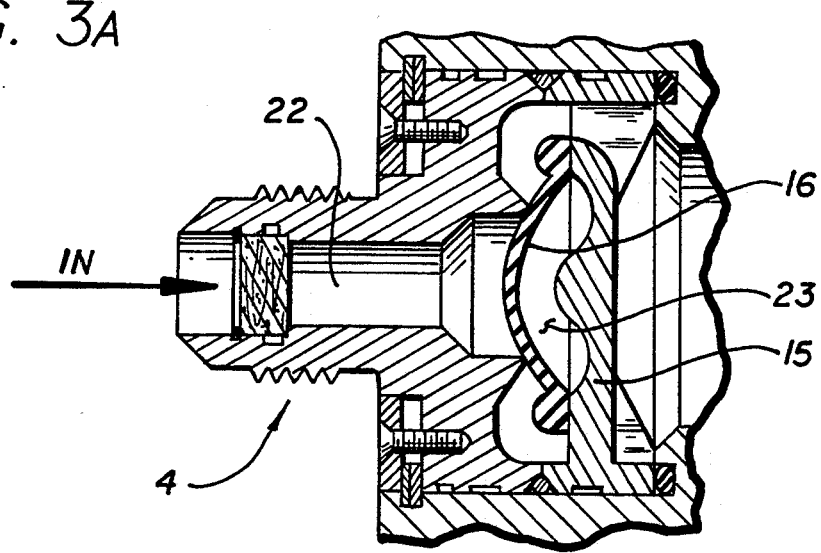
FIG. 3A shows the valving module in a closed condition.
Figure 3B:
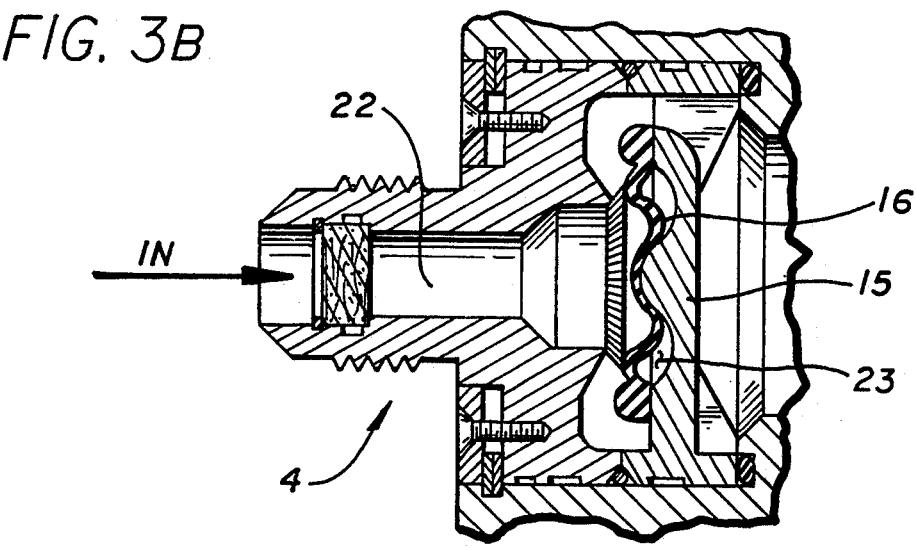
FIG. 3B shows the valving module in modulating (breathing cycle) condition.

The following explains the valving module 4 of the oxygen breathing control of the present invention which is a completely pneumatic module containing no moving parts and provides an excellent seal when fully closed. The valving module 4 comprises an inlet fitting 11, with a sintered bronze filter 12 and an O-ring 13, which is secured by a retaining ring 14, a liner seat 15, the valve liner 16, a valve cage 17, O-rings 18 that prevent an internal and external leakage and a retaining ring 19, which secures all module components in place in the body 1. A plate 20 which incorporates two lobes on its outside diameter is secured to an inlet fitting 11 with two screws 21. The two lobes in the plate 20 nest in two matching cutouts in the body 1. This mechanical engagement prevents rotation of the inlet fitting 11 during tightening of inlet hose. Pressure of 20" $H_2O$ enters the inlet fitting 11 and passes through the 20-micron filter 12. The amount of oxygen flowing through the inlet valve is dependent upon the displacement of the flexible valve liner 16. See FIGS. 3A–3C.

The valve liner 16 moves between the open and closed positions during the breathing cycle due to a change in differential pressure induced across it. This pressure change is derived through the operation of the servo 26 regulator module 6. The flexible valve liner 16 separates the inlet chamber 22 from the control chamber 23 and is finely balanced pneumatically so that a slight change in differential pressure across the chambers will cause it to flex toward either the open or closed operating condition. In this way, the valving module 4 is designed to be sensitive to breathing pressure changes.

At zero pressure in the inlet chamber 22, the valve liner 16 adopts a dome shape and nests inside the valve cage 17. See FIG. 3A. The valve cage 17 incorporates several radial flow slots interposed between flow fins. Oxygen flows through these slots during inhalation. The flow shuts off during exhalation when the valve liner 16 seats over the slots in the valve cage 17. The design of the valve cage 17 is such that the valve liner 16 is fully supported by it when closed. This prevents stretching, rupture or blowout of the valve liner 16. This feature provides long life for the valve liner 16 and enhances accuracy of flow control.

The fins 24 on the outlet side of the valve cage 17 provide directional control of oxygen flow. The fins aid the flow in the event that the valve liner 16 does not flex symmetrically during operation. This, for example, could be caused by a normal uneven thickness of the liner during molding even though the liner is within manufacturing dimensional tolerances. Hence, the valve cage 17 which is provided with the fins help counterbalance the effect of imperfections in the liner.

The inlet valve module 4 is designed to let a maximum of 200 slpm of oxygen flow through the control. When pressure from the first stage regulation module 73 is applied to the inlet chamber 22, the valve liner 16 inverts and comes to rest against the center top of the liner seat 15 as in FIG. 3B. The space between the valve liner 16 and the liner seat 15 forms the control chamber 23 of the control. During the breathing cycle, the valve liner 16 modulates and adopts a balanced condition between the inlet chamber 22 and the control chamber 23.

Figure 3C:
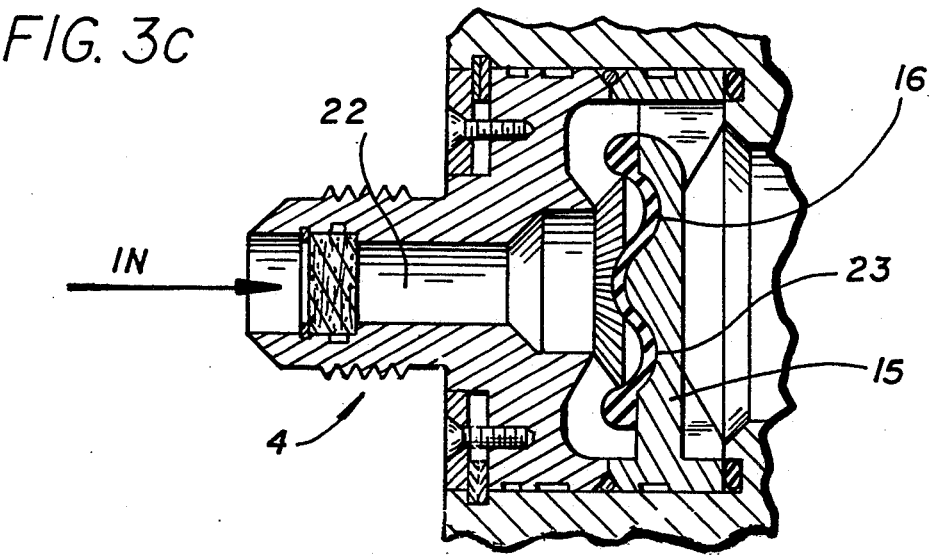
FIG. 3C shows the valving module in an open condition.

During the operation, as the loading pressure in the control chamber 23 is reduced relative to the pressure in the inlet chamber 23, by operation of the servo-regulator module 6, the valve liner 16 rolls off its seating surface on the valve cage 17 allowing more oxygen to flow. In FIG. 3C, the valve liner 16 seats against the liner seat 15 in a fully open condition at maximum flow capacity.

The oxygen breathing control of the present invention provides flow restrictor screw module 5 for adjustment of the pressure differential across the valve liner 16 between the inlet chamber 22 and the control chamber 23. Both the inlet fitting 11 and the liner seat 15 incorporate flow passages 26 and 27 respectively which, through interconnected passages in the body 1, converge in the cavity that contains the flow restrictor screw module 5. The flow through these passages into the control chamber 23 can be varied by an adjustable flow restrictor screw 28.

Further, the function of the flow restrictor screw 28 in combination with the servo regulator module 6 controls inhalation and exhalation response time during the breathing cycle. A pilot regulator valve 29 in the servo regulator module 6 controls the rate at which oxygen in the control chamber 23 bleeds through a pilot pressure passage 25 through the regulator control chamber 30 and into the outlet chamber 31 of the control.

The flow restrictor screw module 5 of FIG. 4 consists of a restrictor screw housing 32, the adjustable flow restrictor screw 28 and three O-rings 33 that prevent leakage of oxygen. The flow restrictor screw 28 is used to adjust flow from the inlet chamber 22 into the control chamber 23 of the inlet valve module 4. The pressure in the control chamber 23 opposes the pressure in the inlet chamber 22 creating a pressure differential across the valve liner 16. The flow restrictor screw 28 is an adjustable needle valve whose tapered tip projects into the flow path from the inlet chamber 22. It is the adjustment of this tip that calibrates the flow to the inlet valve control chamber 23.

Unscrewing the flow restrictor screw 28 permits high volume to flow into the control chamber 23. With this condition the inlet valve will close faster during exhalation but opens slower during inhalation. When screwing in the flow restrictor screw 28, flow to the control chamber 23 throttles and the opposite valve action occurs (the inlet valve opens faster with inhalation but slower during exhalation). Thus, the flow restrictor screw 28 provides a choice of either faster inhalation or faster exhalation during the breathing cycle. The system is balanced to the normal physiological breathing needs of the breather.

Figure 6:
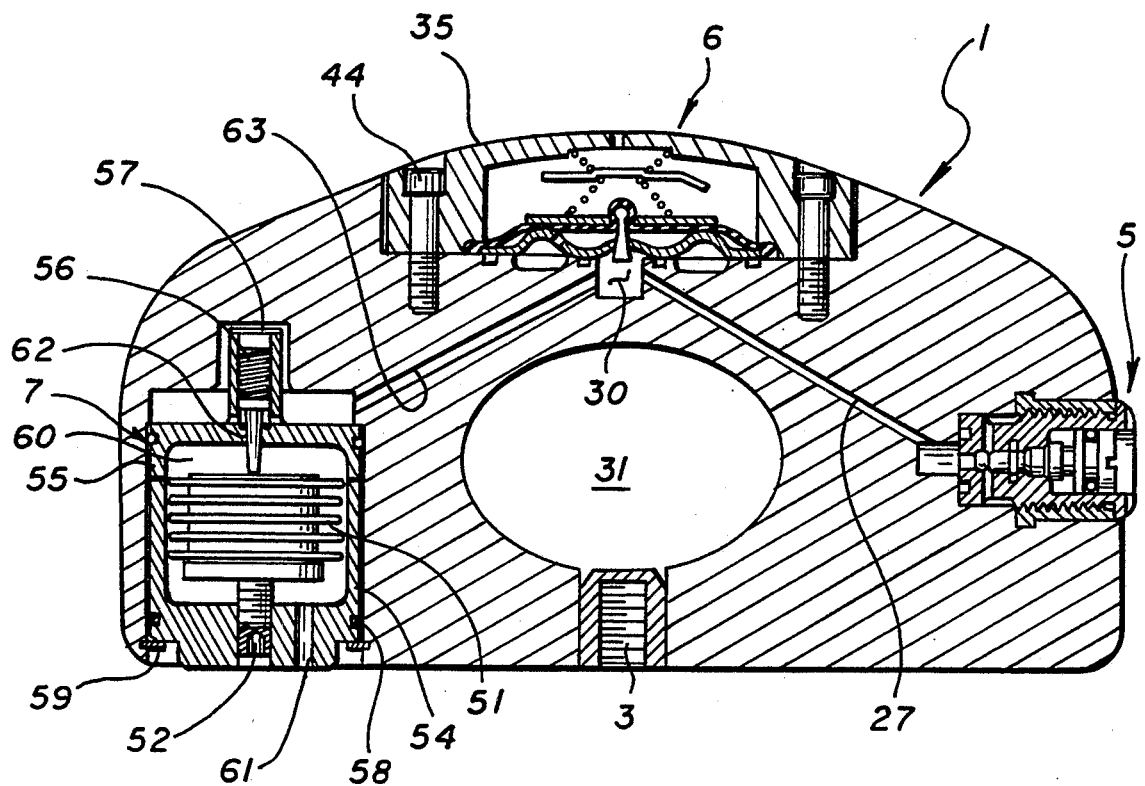
FIG. 6 shows another cross-sectional view of the oxygen breathing control of the present invention showing the servo regulator module and an aneroid module.
Figure 7:
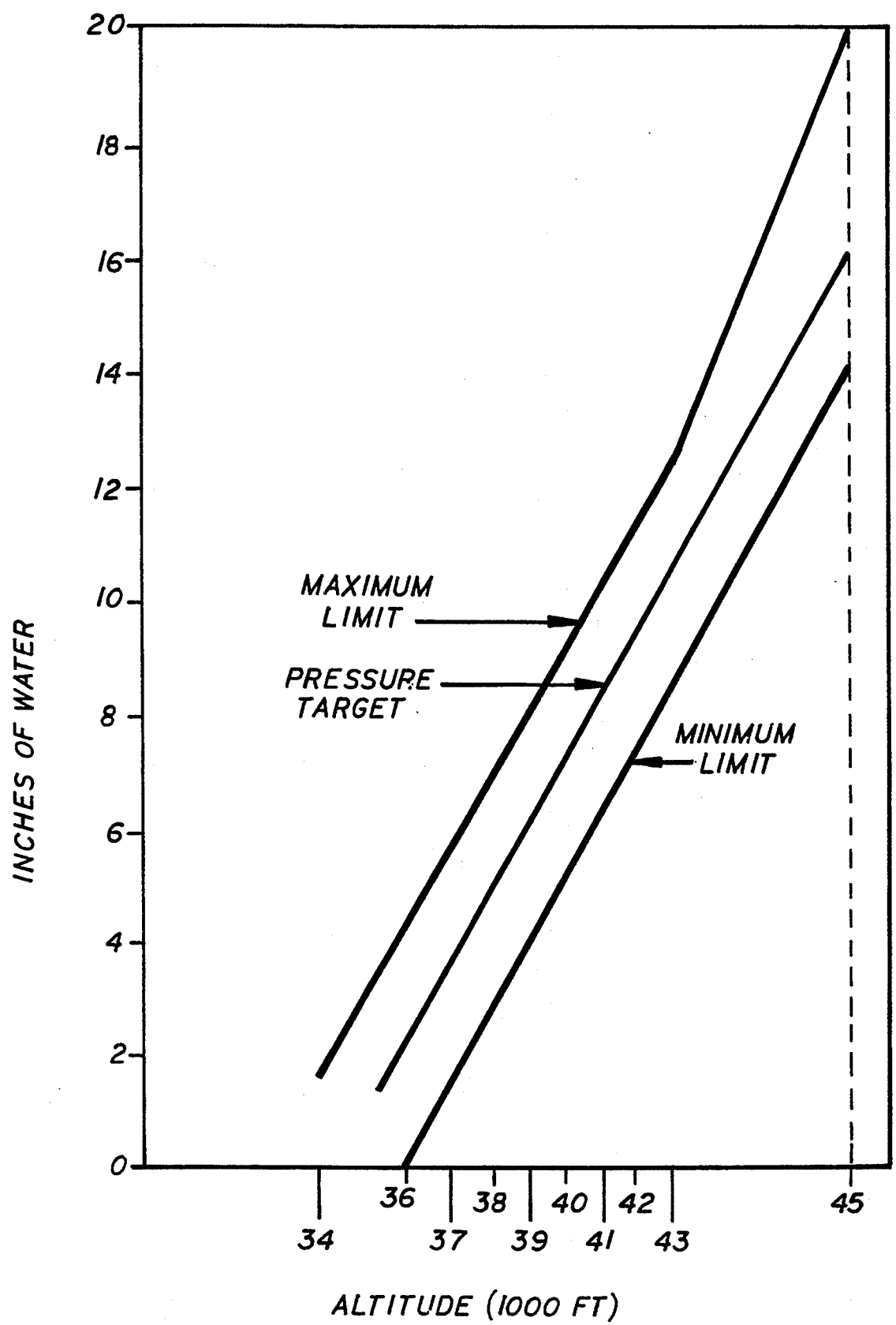
FIG. 7 is a graph of aneroid pressure breathing schedule.

In addition, the flow restrictor screw 28 pneumatically compensates for flow anomalies created by manufacturing dimensional tolerances. The random combination of parts during assembly can affect flow characteristics. For example, the flow passage in one part could be machined to the high end of its manufacturing tolerances while the passage in an interconnecting part could be machined to the low end of its tolerances. The flow anomaly created by such a condition can be corrected via adjustment of the flow restrictor screw 28. This eliminates the need for closer manufacturing tolerances, and subsequent higher manufacturing costs. The flow restrictor screw 28 with an aneroid adjustment screw 52, FIG. 6, is used when calibrating the control to provide proper positive outlet pressure levels at the required altitude. FIG. 7 shows an aneroid pressure breathing schedule graph with pressure in inches (water) on Y-axis and altitude in 1,000 feet on X-axis. Minor adjustments to the slope of the pressure-altitude coordinates are made with the flow restrictor screw 28.

In FIGS. 3 and 4, the servo regulator module 6 comprises a housing 35 that incorporates an atmospheric vent 36, a loading spring 37, an adjustment plate 38, a pilot spring 39, a regulator adjustment screw 40, a diaphragm assembly 41, a diaphragm support 42, two O-rings 43 and four screws 44 which keep the module secured in the body 1. The diaphragm assembly 41 consists of a plate 45, a pilot diaphragm 46 and a tapered stem 47 that are all bonded together. The diaphragm support 42 incorporates an orifice 48 that surrounds the tapered stem 47 and provides pilot regulation of the valve. The diaphragm support 42 also incorporates flow holes 49 that interact with the operation of the pilot regulator valve 29 to pressure balance the inlet valve module 4 during the breathing cycle.

The pilot diaphragm 46 separates and seals the atmospheric chamber 50 from the regulator outlet pressure chamber 31. The adjustment plate 38 is suspended between the loading spring 37 and the pilot spring 39 in the atmospheric chamber 50. The tapered end of the regulator adjustment screw 40 is in direct contact with the edge of the adjustment plate 38. The position of the regulator adjustment screw 40 adjusts the amount of force that the pilot spring 39 imposes on the plate 45 of the diaphragm assembly 41. This in turn adjusts the relative position of the tapered stem 47 inside the orifice 48 of the pilot regulator valve 29. Tightening the regulator adjustment screw 40 lifts the adjustment plate 38 and relieves load on the pilot spring 39. This in turn moves the tapered stem 47 up inside orifice 48 tending to reduce the area of the flow path and consequently reducing the flow of oxygen through it.

The reverse occurs when the regulator adjustment screw 40 is unscrewed out of the housing 1. More force is exerted by the pilot spring 39, forcing the tapered stem 47 down inside the orifice 48 increasing the flow path area, thus allowing more oxygen to flow through the pilot regulator valve 29. The regulator adjustment screw 40 is the means for adjusting pressure regulation of the control. The pilot regulator valve 29 provides fast, accurate and stable pressure regulation during large flow changes, where large pressure reductions are required and where there is considerable variation of inlet pressure to the control.

The servo regulator module 6 of the present invention has a unique bleeding feature which conserves oxygen. A conventional breathing regulator continuously bleeds oxygen to atmosphere between zero to 45,000 feet. As long as the conventional regulator is connected to an oxygen source, such bleeding occurs even if the regulator is not in use.

In contrast, at an altitude of at least up to 34,000 feet, the servo regulator module of the present invention bleeds oxygen internally to the outlet chamber 31 via the outlet pressure sensing port 72 to the breather. In this way, the present invention does not bleed oxygen to atmosphere and waste oxygen supply.

At an altitude of up to 34,000 feet, aneroid module 7 which is pneumatically interconnected with the servo regulator module 6 plays no active role in the operation of the control. The aneroid module 7 comprises an aneroid 51 and an integral adjustment screw 52 enclosed within an upper housing 53 and a lower housing 54, a tapered bleed stem 55, a compression spring 56, a spring seat 57 and two O-rings 58. The aneroid module 7 is connected with the servo regulator module 6 via an aneroid bleed passage 63. A retaining ring 59 keeps the aneroid module 7 in place in the body 1. O-rings 58 prevent external leakage of oxygen. The aneroid 51 in an aneroid chamber 60 is exposed to atmospheric pressure through an aneroid vent 61 in lower housing.

Up to 34,000 feet, force of the compression spring 56 against the tapered bleed stem 55 forces the stem 55 down inside a tapered flow hole 62 preventing flow of venting oxygen into aneroid chamber 60. As altitude increases, the atmospheric pressure imposed upon the aneroid 51 proportionately decreases. The aneroid 51 expands within the aneroid chamber 60 until at 34,000 feet the aneroid makes contact with the tip of the tapered bleed stem 55. At this point the aneroid overrides the normal function of flow regulation controlled by the breather and takes control of the servo regulator module 6.

As altitude increases above 34,000 feet, the aneroid 51 keeps expanding pushing the spring-loaded tapered bleed stem 55 up inside the tapered flow hole 62. This permits flow of oxygen from the regulator control chamber 30 through an aneroid vent passage 63 through the tapered flow hole 62 into the aneroid chamber 60 and out through the aneroid vent 61 to atmosphere.

Volume flow through the tapered flow hole 62 is relative to its cross section flow area which varies due to the changing taper relationship between the bleed stem 55 and the flow hole 62. This area is smallest at 34,000 feet and largest at 45,000 feet due to expansion of the aneroid 51. Since the aneroid bleed mechanism is automatically bleeding the regulator control chamber 30 and the inlet valve control chamber 23 through the aneroid vent passage 63 and the control pressure passage 27, any change in the bleed rate is reflected in the chamber 30. As the bleed rate increases with altitude, pressure in the inlet valve control chamber 23 proportionately decreases. This further opens the inlet valve liner 16 due to relative higher pressure in the inlet chamber 22 and allows increasing oxygen pressure into the outlet chamber 31.

During descent from altitude the aneroid operates in reverse. Reducing flow through the tapered flow hole 62 is reflected by increasing pressure in the inlet valve control chamber 23 and subsequent decreases of pressure to the outlet chamber 31. This activity continues down to approximately 34,000 feet at which point the tapered bleed stem 55 totally closes the tapered flow hole 62 and the aneroid 51 no longer controls positive pressure breathing. At this point inhalation by the breather takes control of the system which now provides flow upon breather's demand.

The aneroid module 7 is primarily responsible for establishing the target pressure shown in the aneroid pressure breathing schedule of FIG. 7. The schedule also shows minimum and maximum pressure limits with respect to altitude. The servo regulator module 6 and the flow restrictor screw module 5 respectively control the pressure within the minimum and maximum limits above 34,000 feet. The altitude start point of 1.5" $H_2O$ pressure at 34,000 feet is established through adjustment of the aneroid adjustment screw 52. The target pressure falling between the maximum and minimum limits shown in the schedule is established through adjustment of the flow restrictor screw 28.

In operation, various modules of the oxygen breathing control function together as follows. With no oxygen pressure at the inlet fitting 11, the valve liner 16 is seated inside the dome shape of the valve cage 17 shutting closed the flow slots in the cage. When an inlet pressure of 1-125 psig (nominally 50 psig) is applied to the first stage regulation module 73, oxygen flows from the inlet chamber 22 through the inlet pressure passages 26, the cavity serving the flow restrictor screw 28, the control pressure passage 27 and into inlet the valve control chamber 23. Pressure differential between the inlet chamber 22 and the inlet valve control chamber 23 is imposed across the valve liner 16, which adopts a balanced condition depending upon pressure differential.

The inhalation and exhalation response time during the breathing cycle is controlled by the adjustable flow restrictor screw 28 which controls the loading pressure in the control chamber 23. Oxygen also flows through the pilot pressure passage 25 into the regulator control chamber 30 of the servo regulator module 6. Thus, the two control chambers 23 and 30 are always at the same pressure. Pressure in the regulator control chamber 30 bleeds through the pilot regulator valve 29, through the flow holes 49 in the diaphragm support 42, through the outlet pressure sensing port 72 into the outlet chamber 31. Until the control chamber 23 senses a change in the loading pressure, the oxygen breathing control remains in this balanced condition. This change is caused by operation of the servo regulator module in response to inhalation and exhalation by the breather. Only a very small change in differential pressure across the valve liner 16 is required to activate desired flow.

Upon inhalation, the pilot diaphragm 46 senses the reduced pressure in the outlet chamber 31, and the diaphragm assembly 41 moves down, opening the pilot regulator valve 2. This in turn bleeds the pressure in the control chamber 23 and into the outlet chamber 31. The pressure reduction in the control chamber 23 changes the differential pressure across the valve liner 16. This causes the valve liner 16 to move away from the flow slots in the valve cage 17 permitting flow through the slots, thereby allowing oxygen to flow into the outlet chamber 31 and to the breather. Amount of flow is regulated by the degree of inhalation. The harder the inhalation, the more the reduced pressure drives open the pilot regulator valve 29 bleeding pressure in the control chamber 23 to the outlet chamber 31. This induces more oxygen of up to 200 slpm to flow through the inlet valve.

During exhalation, the opposite action occurs. Pressure in the regulator control chamber 23 begins to rise simultaneously with pressure rise in the outlet chamber 31. This forces the diaphragm assembly 41 against the opposing force of the pilot spring 39 causing the pilot regulator valve 29 to close (the tapered stem 47 closes the orifice 48). This stops the control chamber 23 from bleeding into the outlet chamber 31. Metered flow from the inlet chamber 22 fills the control chamber 23 causing the valve liner 16 to close over flow slots in the valve cage 17, thereby shutting off flow through the inlet valve. The inlet valve stays in this closed condition until the breather inhales again to start another breathing cycle.

With increasing altitude, the oxygen breathing control delivers a gradually increasing volume of oxygen. Compressed gaseous oxygen will expand as altitude increases while ambient pressure decreases. As altitude increases, the control aneroid 51 keeps expanding until at approximately 34,000 feet it makes contact with the tapered bleed stem 55 in the aneroid chamber 60. The aneroid now overrides the normal function of flow regulation controlled by the breather and takes control of the unit. The oxygen breathing control starts to automatically deliver positive pressure oxygen flow. As altitude increases above 34,000 feet, the aneroid 51 keeps expanding providing positive pressure breathing up to 45,000 feet. At 34,000 feet control breathing pressure is approximately 1.5" $H_2O$, and at 45,000 feet pressure is approximately 20" $H_2O$.

When descending from altitude, the aneroid operates in reverse to the action described above. At 34,000 feet the aneroid 51 relinquishes its role in 100% positive pressure breathing and the control reverts to the flow demand requirements of the breather.

To protect against pressure, the oxygen breathing control of the present invention employs a relief valve module 10 shown in FIG. 6 which comprises a threaded body 64, an O-ring 65, a cap 66, a poppet assembly 67 with a molded rubber seal 68, a compression spring 69, a retainer washer 70 and a retaining ring 71. Under normal breathing conditions, the poppet assembly 67 is closed, and the molded rubber seat 68 seals against the body 1. The retainer washer 70 acts as a guide and retainer for alignment of the compression spring 69. When pressure in the outlet chamber 31 reaches approximately 20" $H_2O$, the poppet assembly 67 cracks open unseating seal 68 from the body 1. This vents the main chamber 31 to atmosphere. The poppet assembly 67 fully opens against the opposing the force of compression spring 69 when pressure in the outlet chamber 31 reaches 30" $H_2O$ providing flow capacity of 250 slpm. O-ring 65 provides the seal between the body 64 and body 1 of the control.

Figure 8:
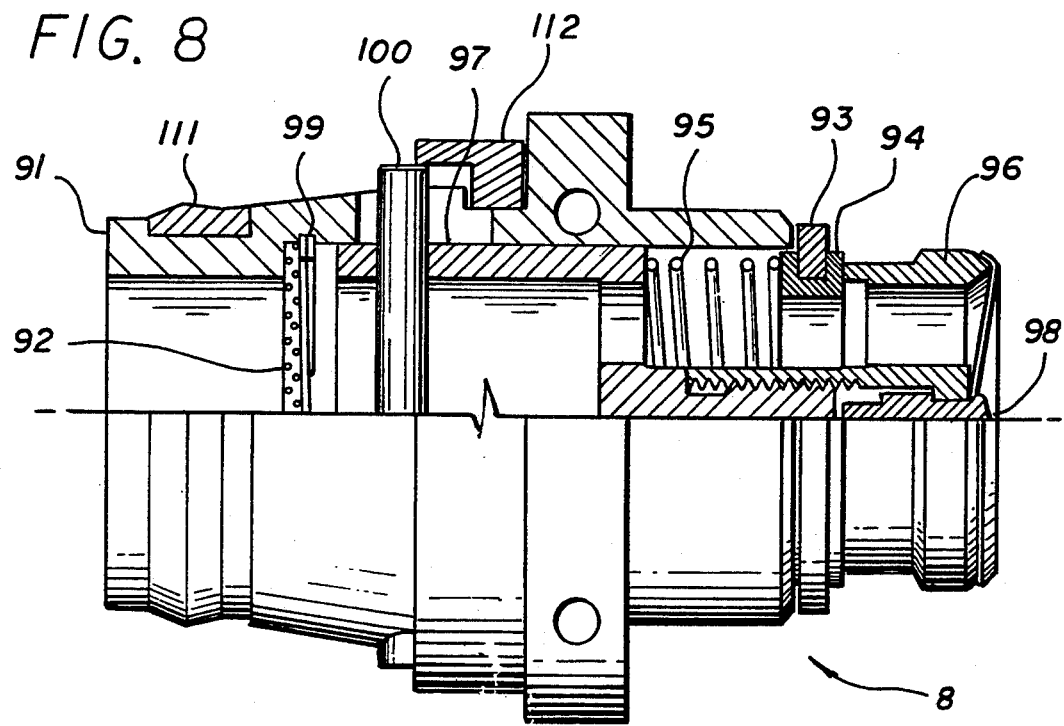
FIG. 8 shows an inlet adapter assembly of the present invention.

The oxygen breathing control of the present invention also employs inlet adapter assembly module shown in FIG. 8 to provide the interface coupling with a 100% portable oxygen console. When uncapped, it provides a flow path for ambient air and acts as an anti-suffocation valve.

A prebreather is connected by an adapter body 91 inserted into and retained by the prebreather interface coupling at the inlet by a retaining ring 111 which snaps into place in a groove in the coupling. 12 to 20 pounds of force is required to engage and disengage the inlet adapter assembly. This coupling action pushes a pin 110 up inside two diametric holes in the body 91. Since the pin 110 is installed across the diameter of an inlet piston 97, the piston 97 is pushed up inside the body 91 against the opposing force of a compression spring 95. Since an inlet valve seat 96 is also mechanically connected to the inlet piston 97, it also is pushed up. This action breaks the seal between the top of a stationary sealing grommet 94 and bottom surface of the inlet valve seat 96, thereby allowing flow of oxygen through the inlet adapter assembly.

The inlet adapter assembly and its prebreather interface coupling are coupled, a gasket 112 provides the seal between the two components. When the inlet adapter assembly is uncoupled from its prebreather interface coupling, a sealing grommet 94 acts as a retainer for a washer 93 and as an internal seal. The washer 93 provides an internal seal between inlet adapter and the body of the control. A retaining ring 99 retains an inlet screen 92 in place in the body 91. The course wire mesh screen prevents large particles of foreign matter from entering the oxygen breathing system.

When the user inhales, a check leaf 98 lifts off the inlet valve seat 96 allowing oxygen to flow through six holes in the valve seat. When the user exhales, back pressure against the top of the check leaf 98 forces the latter to close over the holes.

Inlet adapter assembly also functions as an anti-suffocation valve. When uncoupled from the prebreather, the inlet adapter assembly (with dust cap assembly removed) provides a flow path of ambient air to the control. When the coupling force is removed, compression spring 95 forces the inlet piston 97 and attached inlet valve seat 96 to the closed condition. This creates a seal between the sealing grommet 94 and the seat 96. If the breather depletes his oxygen supply and is unconscious, he can breathe ambient air through the control. During inhalation, the check leaf 98 lifts from inlet valve seat allowing ambient air to flow through the six holes in seat 96. During exhalation, the leaf 98 closes over the holes in seat 96.

The cap assembly 9 of FIG. 4 used with the inlet adapter assembly module 8 serves several functions. It prevents entry of contaminants into the system in storage. When inserted into module 8, it prevents inhalation of smoke into the control during emergency conditions. It also permits breathing of 100% oxygen at less than 34,000 feet altitude, if desired, by preventing entry of ambient air into the control.

The oxygen breathing control of the present invention is also unique in the way the components are constructed in a modular form. This facilitates manufacturing, stocking, assembly and testing of the oxygen breathing controls. For instance, by simply substituting a component in the valving module, the valving module is usable for a different pressure or flow application. The same principle could apply to a relief valve. Simply changing a compression spring in the relief valve could change the opening pressure level.

Having described a preferred embodiment of the oxygen breathing control according to the present invention, it should be apparent that various additional objects and advantages have been attained by the present invention and that a variety of modifications can be made within the scope and spirit of the present invention.

I claim:

1. An oxygen breathing control for supplying an oxygen containing fluid comprising:
    a) a first inlet regulator having:
        an inlet housing having an inlet opening;
        an inlet valve disposed inside the inlet housing near the inlet opening;
        a piston disposed inside the inlet housing downstream of the inlet valve and having a piston chamber; and
        means for opening the inlet valve during inhalation of a user to allow the fluid through to the piston chamber; and
    b) a second inlet regulator coupled with the first inlet regulator and disposed downstream thereof, having:
        an inlet chamber;
        a control chamber disposed downstream of the inlet chamber;
        a valve liner separating the inlet chamber and the control chamber, the valve liner being flexible; and
        means for creating a pressure differential across the inlet chamber and the control chamber and for flexing the valve liner to permit fluid flow upon inhalation.

2. The oxygen breathing control as claimed in claim 1, further comprising means for shutting the fluid flow during exhalation.

3. The oxygen breathing control as claimed in claim 1, further comprising a flow restrictor screw module for restricting the flow between the inlet chamber and the control chamber.

4. The oxygen breathing control as claimed in claim 1 further comprising a servo regulator coupled to the inlet chamber and the control chamber, the servo regulator regulating the pressure differential according to inhalation and exhalation by the user.

5. The oxygen breathing control as chimed in claim 1, further comprising a valve cage near the end of the inlet chamber, the valve cage having a plurality of slots.

6. An oxygen breathing control for supplying oxygen having:
    a) an inlet regulator means for regulating the flow of the oxygen having a piston means for accelerating a rate of the oxygen supply and an inlet diaphragm disposed downstream from the piston, the inlet diaphragm responsive to a pressure differential across the diaphragm;
    b) an outlet chamber; and
    c) a servo regulator module including means for further regulating the pressure of the flow of the oxygen to the outlet chamber having:
        an atmospheric chamber;
        a regulator adjustment screw partially disposed in the atmospheric chamber; and
        a regulator diaphragm coupled to the regulator adjustment screw and disposed in the atmospheric chamber, the regulator diaphragm having a pilot regulator valve, wherein the pilot regulator valve opens when the regulator adjustment screw is unscrewed, and the pilot valve closes when the regulator adjustment screw is tightened.

7. The oxygen breathing control as claimed in claim 6, further comprising means for bleeding oxygen internally to the outlet chamber.

8. The oxygen breathing control as claimed in claim 6, further comprising means for controlling a minimum pressure limit with respect to altitude.

9. The oxygen breathing control as claimed in claim 6, further comprising a flow restrictor screw module for controlling a maximum pressure limit with respect to altitude.

10. The oxygen breathing control as claimed in claim 6, further comprising an aneroid module pneumatically connected to the servo regulator module and establishing pressure of the oxygen supply, having:
    an aneroid chamber defining a flow hole in one wall and a vent in another;
    a bleed stem disposed in the flow hole in the aneroid chamber; and
    a control aneroid disposed in the aneroid chamber, wherein the control aneroid expands and displaces the bleed stem in the flow hole, thereby letting the oxygen flow from the servo regulator module to the aneroid chamber through the flow hole and to atmosphere through the vent.

* * * * *